(12) United States Patent
Karapetyan

(10) Patent No.: US 7,131,982 B1
(45) Date of Patent: Nov. 7, 2006

(54) DENTAL SCALPEL

(76) Inventor: Armen Karapetyan, 1935 N. Van Ness Ave., Los Angeles, CA (US) 90068

( * ) Notice: Subject to any disclaimer, the term of this patent is extended or adjusted under 35 U.S.C. 154(b) by 0 days.

(21) Appl. No.: 11/039,049

(22) Filed: Jan. 20, 2005

(51) Int. Cl.
*A61B 17/32* (2006.01)

(52) U.S. Cl. .................. 606/167; 433/144; 30/340; 30/342

(58) Field of Classification Search ............ 433/10, 433/144; 606/167, 107, 171; 30/236, 329, 30/337–342
See application file for complete search history.

(56) References Cited

U.S. PATENT DOCUMENTS

| | | | | |
|---|---|---|---|---|
| 4,038,986 A | * | 8/1977 | Mahler | 606/132 |
| 4,400,878 A | * | 8/1983 | Vaudreuil | 30/329 |
| 4,682,521 A | * | 7/1987 | Duenas | 82/158 |
| 4,985,035 A | * | 1/1991 | Torre | 606/167 |
| 5,055,106 A | | 10/1991 | Lundgren | |
| 5,423,841 A | | 6/1995 | Kornefeld | |
| 6,413,265 B1 | | 7/2002 | Goodwin | |

* cited by examiner

*Primary Examiner*—Cris L Rodriguez
*Assistant Examiner*—Patrick J. Kilkenny

(57) ABSTRACT

An improved dental scalpel provides a convenient possibility to make accurate surgical operations into oral cavity with the extraordinary access to the different oral cavity areas. An improved dental scalpel includes a coupling device, a handle comprising an opening in the coupling portion of the handle including an inner thread along handle main axis, and a blade portion comprising a blade holder including the coupling portion at the handle side of the blade holder and a blade on another side of the blade holder.

1 Claim, 4 Drawing Sheets

DENTAL SCALPEL

FIELD OF THE INVENTION

This invention relates generally to a device for use in the dental surgery and more particularly to the dental scalpels particularly useful in dental restorations although not specifically limited thereto.

BACKGROUND OF THE INVENTION

Many kinds of scalpels are known and used in dental surgery practice. It is also known that dental scalpels designed for soft tissue surgery typically have thin, elongated handles adapted to hold a blade extending axially from the handle.

The typical surgical scalpel with handle and straight or angled blade can be used to remove excess material from the front (anterior) teeth, because in composite resin restoration of teeth there are often small ledges or overhangs present at the edges of the restorations. Such excess material must be removed from the surface of the tooth and from between adjoining teeth to provide a smooth, hygienic surface, but the anatomic considerations and limited accessibility prevent such an instrument from being used to remove the excess material from the bicuspid or molar teeth in the posterior segment of the mouth.

Many types of oral surgery (e.g. gingival operations, extraction of wisdom-teeth, etc.) cause specific access problems. In these cases it may be difficult to obtain access by means of a common straight scalpel. Sometimes it is necessary to use angled scalpels which are used, for example, in gingival operations.

The known scalpel by U.S. Pat. No. 6,413,265 provides a flat, fairly wide handle to be gripped between the distal phalanx regions of the thumb and the index finger only, and comprises a handle, a blade and a locking mechanism. The handle carries a short cusp blade positioned at acute angles to a horizontal plane (along to axis "X" of the axes coordinate "ZYZ") through the handle and vertical longitudinal ("Y") and transverse ("Z") planes through the handle. The scalpels should be mostly used in pairs with one having a right angled blade and the other a left angled blade in order to enable the dentist to work with both the facial and lingual aspects of the teeth. The flat wide body of the handle is disposed along the horizontal plane. A vertical plane ("Y") passes longitudinally through the handle, and the another vertical plane ("Z") passes transversely through the handle. In accordance with this invention the blade is disposed at an acute angle with respect to the horizontal plane ("X") and at an acute angle also with respect to one or both of the vertical axes ("Y", "Z"). The blade is positioned at an angle with respect to the horizontal plane ("X") of about between 55° and approximately 70°, about between 15° and 30° with respect to the longitudinal vertical plane ("Y"), and 60° and approximately 75° with respect to the transverse vertical plane ("Z"). The handle has a thickened front (or nose) region for securely retaining the blade in the handle. The nose of the handle is provided with an attachment mechanism, by which a blade can be secured to and removed from the handle. This mechanism may has the form of a stud protruding from the nose of the handle and having a non-circular head at its distal end. The blade is provided with an opening sized to slip over the head of stud. The blade is then rotated on the stud in order to engage a stop to become locked beneath the head of the stud.

This scalpel is in some aspects complex, considering the thickened nose region for securely retaining the blade in the handle and the presence of the opening, head and stud. Such scalpel is expensive because it is intended to be disposable, i.e., used on one patient and discarded and, and is not intended to be sterilized repeatedly. Also, the mentioned prior art is not enough elongated for the mouth difficult accessible areas.

Another known scalpel is described in U.S. Pat. No. 5,055,106. This scalpel includes a shank having a holder for releasably mounting a surgical blade. A ball of plastic material is formed by injection molding on the blade proper which consists of metal. The holder includes a sleeve, which is threadedly engaged with the shank at one end thereof and adapted to be screwed axially along the shank. The sleeve forms a ball socket, which is adapted to receive the ball of the blade therein. A clamping rod extends axially within the socket between the shank and the ball to engage and disengage said ball by the sleeve being screwed on the shank. The end of the clamping rod, which is adjacent to the ball, forms a circular sharp edge of a diameter which is smaller than the diameter of the ball, thus cutting into the plastic material of the ball when the sleeve is screwed to engage the clamping rod with said ball. More particularly, the surgical blade comprises a metal portion forming the actual blade (the knife edge), and on this metal portion a plastic body is formed by injection molding, said plastic body forming a neck and a ball. On the shank of the scalpel there is provided for the attachment of the blade a sleeve which forms a spherical ball socket available from the outside through a side aperture. The sleeve has a slot joining the aperture. The sleeve is threadedly engaged with the shank, and for this purpose the shank forms a thicker end portion with a bore having an inside screw thread. The sleeve having an outside screw threadedly engages the inside screw thread of the portion and is displaced axially into and out of the bore by the sleeve being rotated and thus being screwed on the shank. The clamp rod has at the end adjacent the ball socket a circular sharp edge, having a diameter which is smaller than the diameter of the ball. The other end of the clamp rod is engaged with an abutment surface formed by the shank at the bottom of the bore. The ball on the blade can is inserted into the ball socket passing through the side aperture. The ball is a freely rotatable in the ball socket for the adjustment of the blade to a desired rotated or angled position of the neck, being received by the slot at angling, and is locked with the blade in the desired position by screwing the sleeve axially on the shank so that the circular sharp edge of the clamp rod will be engaged with the ball and will cut into the plastic material of the ball. The hardness of the plastic material (e.g. carbon fibre reinforced plastic material) must be chosen such that it is lower than the hardness of the material of the clamp rod, (e.g. metal), so that it is possible for the edge of the clamp rod to cut into the material.

Such scalpel has the complex design (construction), has many components that creates the difficulties for satisfied sterilization (the dirt collected between components has to be thorough cleaned/removed), and inconvenient considering necessity of compatibility of the material hardness (e.g. the hardness of the plastic material /carbon fibre reinforced plastic material/ must be chosen such that it is lower than the hardness of the material of the clamp rod /metal/, so that it is possible for the edge of the clamp rod to cut into the material).

The other surgical cutting devices are well known in the medical practice. For example, U.S. Pat. No. 5,432,841, describes the surgical device comprising a handle, a blade rotatably mounted to the handle's distal end, and a controller on the handle for manually positioning the blade at a desired angular position during movement of the handle. More specifically, the surgical instrument comprises a handle, a latching mechanism, a controller and a blade. The handle includes two opposing walls joined at their proximal ends and separated at their distal end to form two blade holding jaws. The opposing walls of the handle are paralleled to each other. Also, the handle includes two platforms placed approximately two-thirds of the distance away from the distal ends on both walls, and a band placed between the jaws in order to prevent the jaws from separating a large amount. The band 24 (a metal spring) functions to prevent an excessive opening of the jaws in the disengaged position and serves to keep the walls in the proper orientation as they move past one another during the procedure. The band also acts as a spring which encourages the opening of the jaws in the disengaged position. It is the spring of metal band and the handle which is the opposing force to the latching mechanism providing a secure hold on the cylindrical shaft, which in turn secures the blade.

The jaws of the handle have two positions—a disengaged and engaged position. In the disengaged position the handle's jaws are held together before the handle engages the blade by a cap which is an auxiliary equipment and fits over the distal most tip portions of the jaws. Both jaws also contain orientation marks on their surface which helps align the blade with the handle. The orientation marks on the top surface of the jaws and form a straight line which is perpendicular to the long axis of the instrument when the instrument is in its engaged position. In use, the jaws are placed within the jaw cap, which allows the jaws to separate the proper amount so that the blade can fit up between their inner surfaces. The jaws are brought down over the blade in such a way that the orientation marks of the jaws form a line with the orientation mark on the top surface of blade. The orientation mark of the blade provides the proper placement of the blade into the jaws. The orientation marks on the jaws are placed at a distance from the distal end of the jaws which ensures the safe rotation of the cylindrical shaft of the blade between the inner surfaces of the jaws.

The latching mechanism consists of a slot, a receiver, and a securing member. The receiver is a rolling mechanism which consists of a cylinder and a bracket mounted on wall. The cylinder rolls on a pivot pin which is placed through the longitudinal axis of the cylinder and secured to each end of the bracket. The device also has some complex modifications described in the mentioned above patent.

This surgical device has the same deficiencies, i.e. the complex design (construction), has many components that creates the difficulties for satisfied sterilization (the dirt between components has to be thorough cleaned/removed), and inconvenient for surgeon considering its irregular form and necessity to change blade angle during surgical procedure.

The another scalpel with the adjustable blade is described in U.S. Pat. No. 4,672,964. The scalpel includes a handle, at the distal end of which is threaded a chuck housing, in which a chuck is adjustably held to the chuck housing and in which a blade is removably held. The chuck is arranged within the chuck housing to pivot within the range of a right angle or 90°, while the chuck and blade can rotate as a unit clockwise and counter-clockwise about the vertical axis ("Y") of the blade. Also, the handle comprises the shaft, slot, crank head, retaining pin, groove, finger ridge, a locking rods, locking crank. The locking crank comprises a lever arm. The shallow recesses are formed in both the forward and rear edges of the crank head, respectively. The retaining pin passes through an enlarged hole formed in the crank head. Additionally, this scalpel has many other components (not described hereinto) coupled with the parts mentioned above.

The described surgical device is a complex and expensive scalpel requiring many controlling operations.

Thus, there is a great need in the art for the improved not complex, not expensive and reliable dental scalpel, providing the possibility of the convenient surgical procedure in the difficult accessible mouth areas.

OBJECT AND ADVANTAGES OF THE INVENTION

Accordingly, several objects and advantages of the present invention are to provide convenient, effective, reliable, not complex and not expensive dental scalpel.

It is another object of the invention to eliminate necessity to change the angles of the blade.

It is still another object of the invention to reduce the complexity of the dental surgical instrument allowing the extraordinary access in different dental surgical operations of any type.

It is further object of the invention to provide not thick and not short dental scalpel of the convenient form in order to avoid the necessity of the dental surgeon finger placement into patient's oral cavity.

Still, further objects and advantages will become apparent from a consideration of the ensuing description accompanying drawings.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

An improved dental scalpel provides a convenient possibility to make accurate surgical operations into oral cavity.

Many types of oral surgery (e.g. gingival operations, extraction of wisdom-teeth, etc.) cause specific access problems. In these cases it may be difficult to obtain access by the known scalpels. It may be necessary to use angled scalpels or reversed knives which are used for example in gingival operations. The improved scalpel provides an extraordinary access in the different surgical operations of any type including the dental surgical operations.

An improved dental scalpel includes a coupling means, a handle, comprising an opening in the coupling portion of the handle including an inner thread along handle main axis, and a blade portion, comprising a blade holder the coupling portion of which includes an outer thread at the handle side of the blade holder, and a blade on another side of the blade holder. The coupling handle with the blade holder is provided by the coupling means of two embodiments.

DESCRIPTION OF THE PREFERRED EMBODIMENTS

Herein the description of an improved dental scalpel will be done in statics (as if the components of the improved device are suspended in the space) with description of their relative connections to each other. The description of the functional operations of an the improved denta scalpel will be done hereinafter.

Figure 1A:
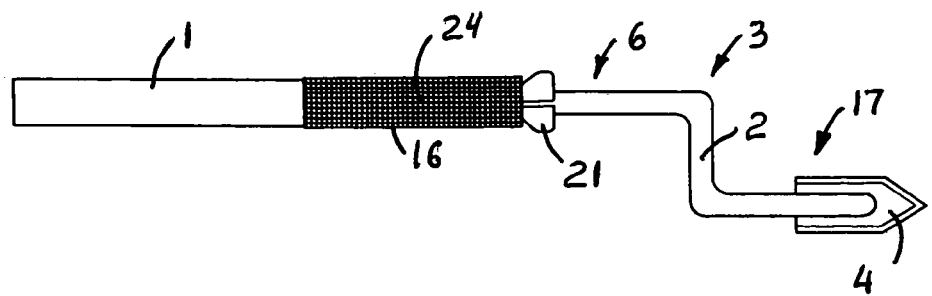
FIGS. 1a, 1b are the simplified drawings of the first embodiment of the improved dental scalpel.
Figure 1B:
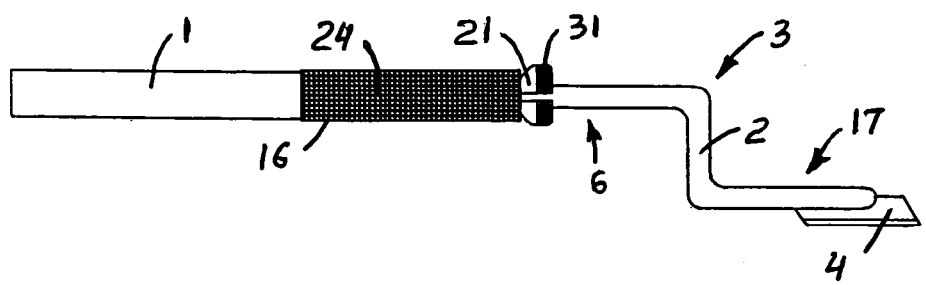
Figure 2:
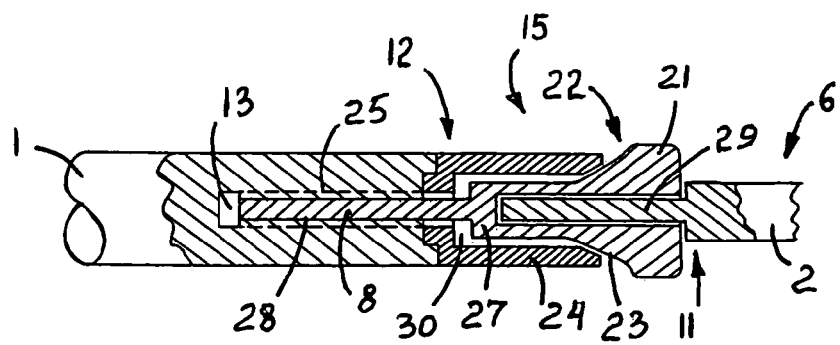
FIG. 2 is a simplified drawing of the first embodiment of the coupling means of the improved dental scalpel.
Figure 5:
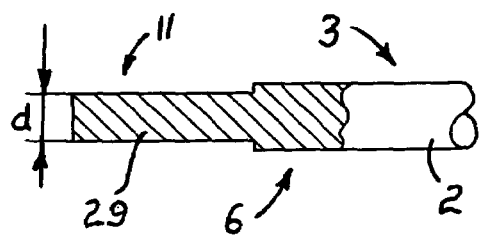
FIG. 5 is a simplified drawing of the first embodiment of the coupling portion of the blade holder.
Figure 6:
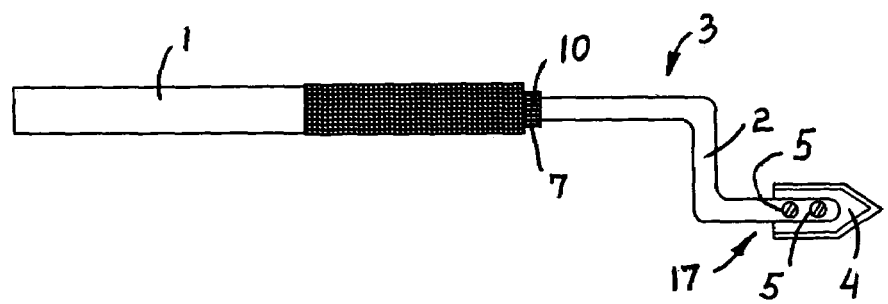
FIG. 6 is a simplified drawing of the another embodiment of the improved dental scalpel.

Referring to FIGS. 1a, 1b, 6, the improved dental scalpel comprises a handle 1 coupled with the blade holder 2 of the blade portion 3. The blade portion 3 comprises a blade holder 2 and a blade 4. Also, the improved scalpel includes the coupling means 15 (see FIGS. 2, 7) comprising the coupling portion 11 (see FIGS. 5, 9) of the blade holder 2 and the coupling portion 12 of the handle 1 (see FIGS. 3, 8).

Figure 3:
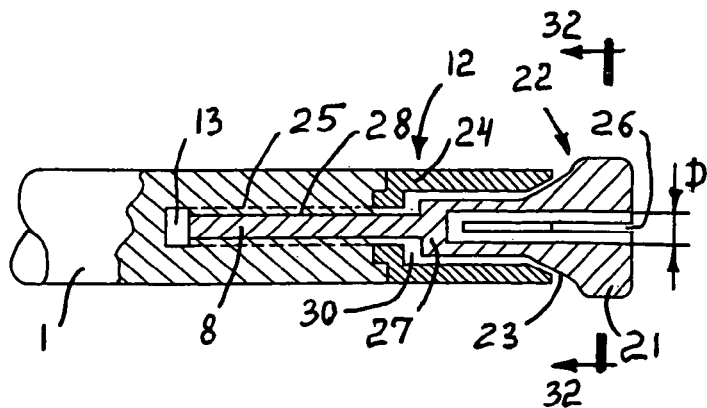
FIG. 3 is a simplified drawing of the first embodiment of the coupling portion of the handle.
Figure 4:
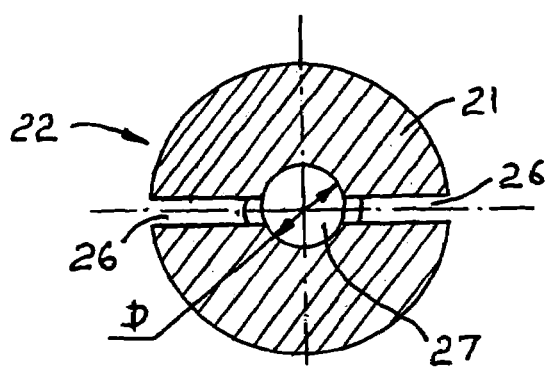
FIG. 4 is a cross-sectional view 32—32 of the clamping head.

As it is shown in FIG. 3, the coupling portion 12 of the handle 1 can include, the opening 13, which comprises the inner thread 25, a cylindrical tightening ring 24 and circular clamping means 22 (a.k.a. ring clamp) including at least two slits 26 in the body 27, conic portion 23 and head 21 on one side of its body 27, and the outer thread 28 on the another side of its body 27. The cross-sectional view of the head 21 is shown in FIG. 4. The coupling portion 11, shown in FIG. 5, is located on the handle side 6 of the blade portion 3 can comprise the inserting portion 29 of the blade holder 2. The inserting portion 29 includes the outer diameter "d" slightly smaller than the inner diameter "D" of the clamp opening 30 (see FIGS. 3–5). The tightening ring 24 of the coupling portion 12 can comprise the texture 16 on the outer surface in order to increase friction between surgeon fingers and handle 1 during surgical procedure, and to increase friction between fingers and handle 1 during the handle 1 and blade holder 2 coupling. Also, the tightening of the coupling means 12 can be provided by the rotation of the slitted head 21 The inner side of the tightening ring 24 may include a slightly textured surface/not show/in order to provide better contact with the outer surface of the body 27 of clamping means 22 during rotation of the tightening ring 24. The outer surface of the head 21 may include the texture 31, as shown in FIG. 1b.

Figure 7:
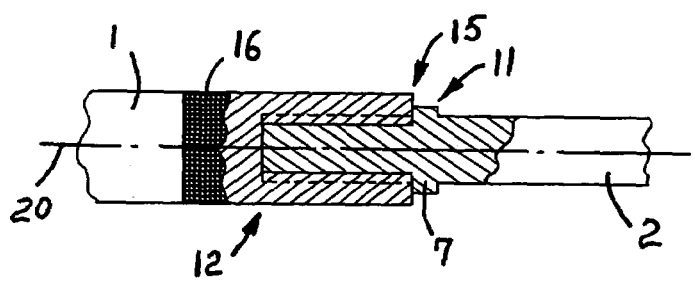
FIG. 7 is a simplified drawing of the another embodiment of the coupling means of the improved dental scalpel.
Figure 8:
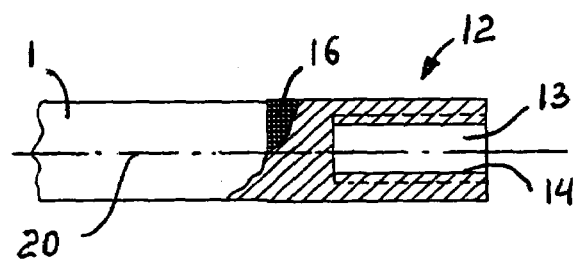
FIG. 8 is a simplified drawing of the another embodiment of the coupling portion of the handle.
Figure 9:
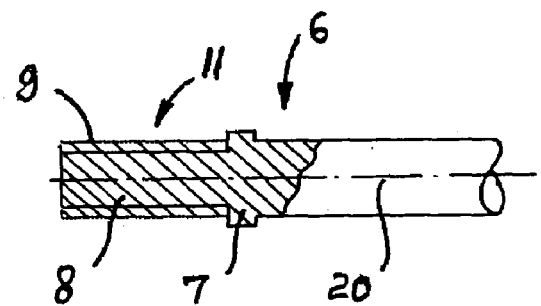
FIG. 9 is a simplified drawing of the another embodiment of the coupling portion of the blade holder.

Referring to FIGS. 6, 7, 9, the coupling portion 11 located on the handle side 6 of the blade portion 3 comprises the tightener 7 and the threaded portion 8 of the blade holder 2. The threaded portion 8 includes the outer fine thread 9. The tightener 7 includes the texture 10 on its outer surface in order to increase friction between fingers and tightener 7 during the handle 1 and blade holder 2 coupling. The coupling portion 12 (shown in FIG. 8) of the handle 1 includes the opening 13 which includes the inner fine thread 14. The coupling portion 12 of the handle 1 comprises the texture 16 on the outer surface in order to increase friction between surgeon fingers and handle 1 during surgical procedure, and to increase friction between fingers and handle 1 during the handle 1 and blade holder 2 coupling. The use of the fine thread (the pair "outer fine thread 9—inner fine thread 14") provides the reliable connection of the blade portion 3 to the handle 1. Some simple fixing means (not shown) to fix the threaded portion 8 of the blade holder 2 into the threaded opening 13 of the handle 1 can be used.

Figure 10:
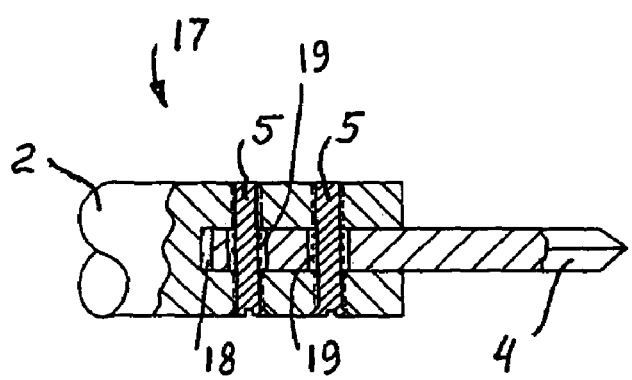
FIG. 10 is a simplified top views of the blade side of the blade holder in compliance with FIGS. 1, 6.

According to FIG. 10, the blade side 17 of the blade portion 3 includes the blade opening 18 intended for the blade 4 insertion. The blade holder 2 also can comprise the threaded apertures 19 for the connection of the blade holder 2 and blade 4 (inserted in the blade opening 18) by the screw(s) 5 (in FIG. 6 it is conditionally shown two screws 5, but it may be used at least one or any reasonable quantity of the screws). The connection of the blade holder 2 with the blade 3 can be provided by any reasonable means instead of the screw(s) 5, for example, by rivet(s) (not shown) or can be welded (not shown) to each other, etc. In the case, when the blade 3 is welded (riveted) to the blade holder 2 or molded into the blade holder 2, the entire piece (blade holder and blade) will be replaceable instead of the blade 4 only when they are connected to each other, for instance, by the screw(s) or, for example, by removable pin(s) (not shown).

Figure 11A:
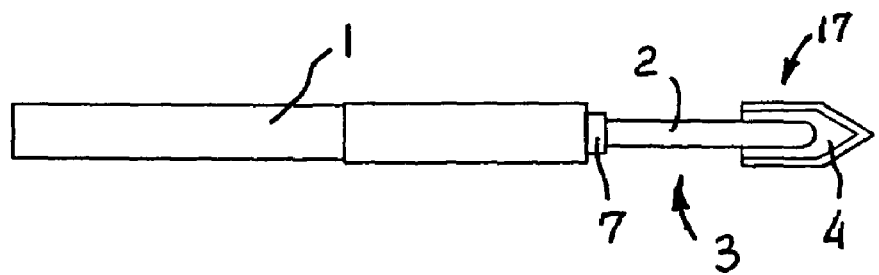
FIGS. 11a–11c are the simplified different configurations of the blade holder portion.
Figure 11B:
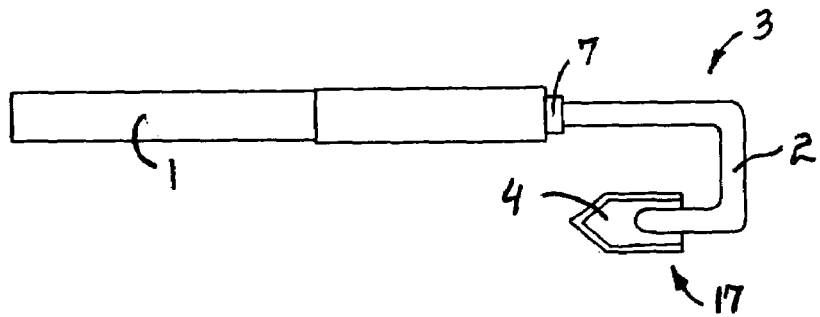
Figure 11C:
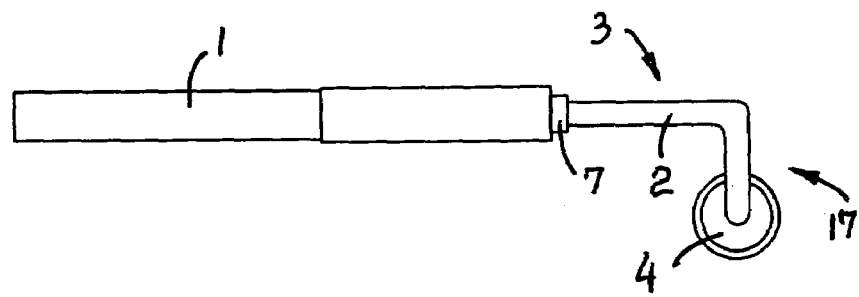

The different configurations of the blade holder 2 are shown in FIGS. 11a–11c, but these configurations are not limited by the present embodiments and can be of any necessary and reasonable geometrical form (shape), size, color, etc., and are not limited by the presentations made in the drawings. Also the blade can be of any necessary shape (form), as for example, the blade in FIG. 11c is shown of the circular form (shape).

Figure 12A:
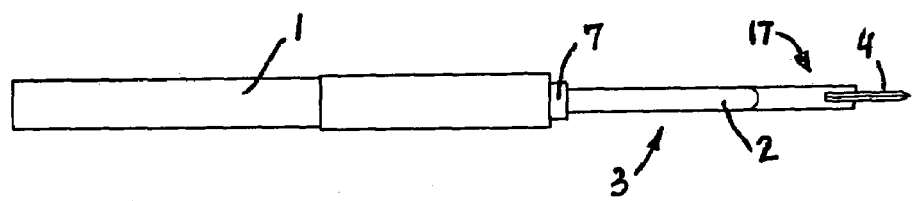
FIG. 12a is a simplified top view of the improved dental scalpel in compliance with FIG. 6.
Figure 12B:
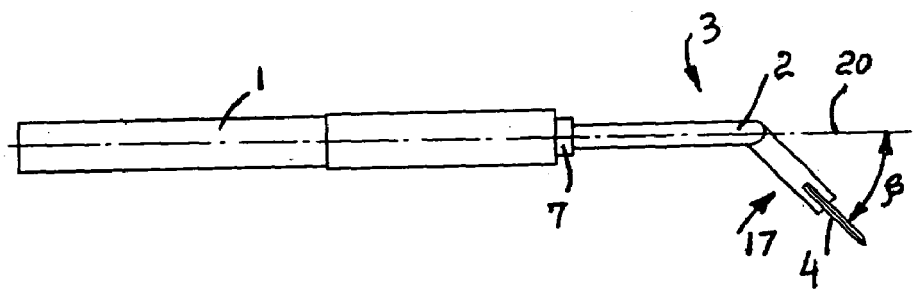
FIG. 12b is a simplified top view of the improved dental scalpel with the angled blade side of the blade holder.

In FIG. 12a is shown a top view of the improved dental scalpel presented in FIG. 6. The blade side 17 of the blade holder 2 can be unchangeably directed at any desired or necessary angle "β" from 0° to 360°, as shown in FIG. 12b (e.g. for the configuration shown in FIG. 11b the angle "β" is 180°).

All components can be made of any medically reasonable material. For example, the handle 1 and the blade portion 3 (except the blade 4) can be made of an inexpensive material, such as plastic, that can be cast or molded. Also, the handle 1, the blade portion 3 and the blade 4 can be made of the stainless steel, carbon steel or surgical steel under conditions of sterilization possibility for the repeated use, if they are not considered as disposable, and not hazardous for human health. The textures 10 and 16 can be of any reasonable pattern and are not limited by the presentations made in the drawings.

During any surgery the surgeon uses many surgical devices, and at any moment he/she can choose the exactly needed scalpel of a plurality of the scalpels (set of the improved scalpels) on the dental surgeon's tray (surgical desk). Hence, the blade portion may be removed from the handle to be replaced by blade handle of different shapes and sizes to enable the surgeon to manipulate the scalpel into smaller confined spaces, once the blade holder is connected to the handle it is not movable with respect to the handle. As has been mentioned above, some scalpels are pivotable in the chuck in order to direct the blade plane at the desired angle, but they are complex, expensive, cleanless (considering many components and their connections to each other), and are practically not reliable.

Due to such improved dental scalpel configurations the incision in all oral regions will be facilitated, the extreme access in the oral cavity and other cavities in the body will be achieved. The dental surgical scalpel of the this invention due to the fact that the blade holder and handle thereof can be made of reliable plastic material formed thereon by injection molding can be manufactured at very low costs so that these portions of the scalpel are a cheap one-way product and thus can be replaced at low costs when necessary.

CONCLUSION, RAMIFICATION AND SCOPE

Accordingly the reader will see that, according to the invention, I have provided a device for dental surgical procedures, providing convenient, not complex and not expensive dental scalpel. An improved dental scalpel has various possibilities, considering activities of the dental practice.

While the above description contains many specificities, these should be not construed as limitations on the scope of the invention, but as exemplification of the presently-preferred embodiments thereof. Many other ramifications are possible within the teaching to the invention. For example, an improved scalpel can successfully be used in ophthalmology and eliminates the necessity of the surgeon to control (adjust) the direction of the blade. The improved dental scalpels are proposed to allow the extraordinary access into oral cavity during the different dental surgical operations of any type.

The present invention has been described in accordance with a preferred embodiment and variations thereof. One of ordinary skill will be able to effect changes to the disclosed embodiments, various substitutions of equivalents, and other alterations without departing from the broad concepts disclosed.

Thus, the scope of the invention should be determined by the appended claims and their legal equivalents, and not by examples given.

THE DRAWING REFERENCE NUMERALS

1.—a handle;
2.—a blade holder;
3.—a blade portion;
4.—a blade;
5.—a screw;
6.—a handle side of the blade portion;
7.—a tightener;
8.—a treaded portion of the blade holder;
9.—an outer fine thread;
10.—a textured surface of the tightener;
11.—a coupling portion of the blade portion;
12.—a coupling portion of the handle;
13.—an opening;
14.—an inner fine thread;
15.—a coupling means;
16.—a textured surface of the handle;
17.—a blade side of the blade holder;
18.—a blade opening;
19.—an aperture;
20.—a main axis;
21.—a head;
22.—a circular clamping means;
23.—a conic portion;
24.—a tightening ring;
25.—an inner thread;
26.—a slit;
27.—a body;
28.—an outer thread;
29.—an inserting portion;
30.—a clamp opening;
31.—a texture of the head;
32—32 is a cross-sectional view.

What is claimed is:
1. An improved dental scalpel comprising
a handle including
a coupling portion of said handle comprising
an opening along a main axis;
an inner thread of said opening located along said axis;
a cylindrical tightening ring comprising a texture located on the outer surface of said cylindrical tightening ring;
a circular clamping means including at least two slits in a body, wherein said body comprises
a conic portion and a head located on one side of said body, and wherein said head comprises the textured outside surface;
an outer thread located on the another side of said body, and wherein said outer thread is intended for coupling with said inner thread of said opening;
a blade portion including
a blade holder of elongated configuration with the cross-sectional dimension lesser than cross-sectional dimention of said handle comprising
an inserting portion of cylindrical configuration and located at a handle side of said blade holder, and wherein an outer diameter of said inserting portion is smaller then an inner diameter of a clamp opening;
a surgical blade located at a blade side of said blade holder.

* * * * *